US00PP26174P3

(12) United States Plant Patent
Bacon

(10) Patent No.: US PP26,174 P3
(45) Date of Patent: Dec. 1, 2015

(54) PLUM TREE NAMED 'SUPLUMFORTYSIX'

(50) Latin Name: *Prunus salicina*
Varietal Denomination: Suplumfortysix

(71) Applicant: Sun World, International LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 103 days.

(21) Appl. No.: 13/998,140

(22) Filed: Oct. 7, 2013

(65) Prior Publication Data

US 2015/0101088 P1 Apr. 9, 2015

(51) Int. Cl.
*A01H 5/08* (2006.01)

(52) U.S. Cl.
USPC ..... Plt./184
CPC ..... *A01H 5/0862* (2013.01)

(58) Field of Classification Search
USPC ..... Plt./184
See application file for complete search history.

*Primary Examiner* — Keith O. Robinson

(74) *Attorney, Agent, or Firm* — Knobbe, Martens, Olson & Bear, LLP

(57) ABSTRACT

A new and distinct plum tree variety, *Prunus salicina,* cv. 'Suplumfortysix' is characterized by a dark-purple dappled skin.

1 Drawing Sheet

Latin name of the genus and species claimed: *Prunus salicina.*

Variety denomination: 'Suplumfortysix'.

BACKGROUND AND SUMMARY OF THE INVENTION

This invention relates to the discovery and asexual propagation of a new and distinct variety of plum, *Prunus salicina* cv. 'Suplumfortysix'. The new variety was first originated by hybridization on Aug. 5, 2007 by Terry A. Bacon as breeder number: 'PL878RZ'.

The new variety 'Suplumfortysix' is characterized by a dark purple dappled skin.

The seed parent is '96P024-003-430' (unpatented), and the pollen parent is unknown. The parent varieties were first crossed in February 2004, with the date of first sowing being February 2005, and the date of first flowering being February 2007. The new plum variety 'Suplumfortysix' was first asexually propagated by Terry Bacon near Wasco, Kern County, Calif. in January 2010, by grafting.

The new variety 'Suplumfortysix' is distinguished from its seed parent in that the new variety ripens about 18 days after '96P024-003-430' and has a dark purple dappled skin color compared to solid black skin for '96P024-003-430'.

The new variety 'Suplumfortysix' ripens about 20 days before 'Angeleno' (U.S. Plant Pat. No. 2,747) and has a dark purple dappled skin compared to the solid reddish-black skin of 'Angeleno' (U.S. Plant Pat. No. 2,747). The new variety Suplumfortysix' ripens about 14 days after 'Dapple Dandy' (U.S. Plant Pat. No. 9,254) and has a dappled finish like 'Dapple Dandy' (U.S. Plant Pat. No. 9,254) but the color of the new variety is a dark-purple dappled finish compared to the pale-reddish dapple of 'Dapple Dandy.'

The new variety 'Suplumfortysix' has been shown to maintain its distinguishing characteristics through successive asexual propagations by, for example, grafting.

BRIEF DESCRIPTION OF THE PHOTOGRAPH

The accompanying color photographic illustration shows typical specimens of the foliage and fruit of the present new plum variety 'Suplumfortysix'.

The illustration shows the upper and lower surface of the leaves, a view of the fruit as a whole, an exterior and sectional view of a fruit divided across its suture plane to show flesh color, pit cavity and the stone remaining in place in a 4 year old plant.

The photographic illustration was taken shortly after being picked and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to a 4 year old 'Suplumfortysix' plants on Nemaguard rootstock, grown in the vicinity of Wasco, Kern County, Calif., during 2013, and is believed to apply to plants of the variety grown under similar conditions of soil and climate elsewhere.

TREE

General: (Measurements taken on a 4 year old tree unless otherwise noted.)

*Size.*—Medium. Reaches a height of approximately 3 meters with normal pruning.

*Spread.*—Approximately 3 meters.

*Vigor.*—Medium.

*Growth.*—Semi-upright.

*Productivity.*—Productive.

*Form.*—Vase formed.

*Bearer*.—Regular.
*Fertility*.—Unknown.
*Canopy density*.—Medium.
*Hardiness*.—Hardy in all fruit growing areas of California. Winter chilling requirement is approximately 700 hours at or below 7.2 C.
*Disease resistance/susceptibility*.—Under close observation in Kern County, Calif., no particular plant/fruit disease resistance/susceptibility has been observed.
*Insect resistance/susceptibility*.—Under close observation in Kern County, Calif., no particular plant/fruit insect resistance/susceptibility has been observed.

Trunk: (Measurements at approximately 30 cm above soil line on mature tree).
*Length*.—Approximately 61 cm.
*Diameter*.—Approximately 14 cm.
*Texture*.—Medium shaggy, increases with age of tree.
*Trunk color*.—About Medium Grey-Brown 199B to Medium Greyed-Orange 173B; becomes darker with age.

Branches: (Measurements at approximately 90 cm above soil line.)
*Length*.—Approximately 240 cm.
*Size*.—Diameter approximately 9 cm.
*Texture*.—Medium, Shaggy.
*Color*.—Varying between about Medium Grey-Brown 198B to Medium Greyed-Orange 173B; becomes darker with age.
*Lenticels*.—Present.

Lenticels:
*Density*.—About 2/cm$^2$.
*Color*.—About Medium Grey-Brown 199B.
*Size*.—Medium, about 1 mm×2mm.
*Length*.—3 mm.
*Width*.—2 mm.

Flowering shoots: (Data taken in September at mid-point of current season growth.)
*Size*.—Average diameter approximately 4 mm.
*Color*.—Topside: About Dark Greyed-Orange 176A. Underside: About Dark Greyed-Orange 176A.
*Internode length*.—Medium; approximately 2 cm. Midway on flowering shoot.
*Flowering shoot lenticels*.—Medium, about 8/cm2. Color: About Medium Greyed-Orange164B. Diameter: Approximately 0.5 mm. Texture: Smooth.
*Flowering shoot leaf buds*.—Shape: Conical. Width: Approximately 1.5 mm. Length: Approximately 2 mm. Color: About Dark Greyed-Orange 166A. Texture: Smooth.
*Flowering shoot flower buds*.—Shape: Ovoid. Width: Approximately 1.1 mm. Length: Approximately 2 mm. Color: About Dark Greyed-Orange 166A. Number of buds per node: Usually 2-4. Texture: Smooth.
*Density of flower buds*.—Medium, about 2-4/node.
*Density of leaf buds*.—Medium, about 1-4/node.
*Flower bud distribution*.—On spurs and one year old shoots and older wood.
*Ratio of wood (leaf) buds to flowering buds*.—2/2 on nodes.
*Anthocyanin intensity*.—None or very slight.

FOLIAGE

Leaves: (Data taken in September on fully expanded leaves at mid-point of the current season growth).
*Size*.—Medium.
*Average length*.—Medium; approximately 80 mm without petiole.
*Average width*.—Medium; approximately 43 mm.
*Thickness*.—Medium, about 0.8 mm.
*Color*.—Upper surface: About Dark Yellow-Green 147A. Lower surface: About Medium Yellow-Green 148C.
*Form*.—Broad obovate.
*Tip*.—Cuspidate.
*Base*.—V-shaped.
*Margin*.—Crenate.
*Venation*.—Pinately net veined.
*Vein color*.—About Dark Yellow-Green 147D.
*Surface texture*.—Smooth (upper and lower).
*Leaf blade (ratio of length to width)*.—Medium, About 2:1.
*Shape in the cross section*.—Concave.
*Angle at apex*.—Small.
*Profile*.—Up folded.
*Leaf blade tip*.—Curved downwardly.
*Angle of tip*.—Acute.
*Undulation of margin*.—Slight.

Petiole:
*Texture*.—Smooth.
*Strength*.—Strong.
*Average length*.—Medium; approximately 13 mm.
*Average diameter*.—Approximately 1.5 mm.
*Color*.—About Light Yellow-Green 147D.
*Thickness*.—Medium, About 1.1 mm.

Stipules:
*Texture*.—Smooth (upper and lower surfaces).
*Number/leaf bud*.—Approximately 0-2 per leaf bud when present.
*Typical length*.—Approximately 8 mm.
*Color*.—About Medium Yellow-Green 147C.
*Persistence*.—Falls off.

Leaf glands:
*Form*.—Globose.
*Average number*.—0-2.
*Position*.—On leaf base, opposite.
*Average size*.—Medium; approximately 0.5 mm.
*Color*.—About Dark Greyed-Orange 165A.

FLOWERS

General:
*Flower blooming period*.—First bloom: Approximately Mar. 1, 2013 in Wasco, Calif. Full bloom: Approximately Mar. 4, 2013 in Wasco, Calif.
*Location of first bloom*.—Top of tree.
*Location of full bloom*.—Mid-section of the canopy.
*Time of bloom*.—Medium from approximately March 1-March 4.
*Duration of bloom*.—Medium; approximately 14 days.
*Diameter of fully opened flower*.—Medium, approximately 7 mm.
*Flower aroma*.—Slight aroma.
*Shape*.—Rosaceous.

Peduncle:
*Strength*.—Strong.
*Length*.—Medium; approximately 12 mm.
*Diameter*.—Slender; approximately 1.5 mm.
*Color*.—About Medium Yellow-Green 144B.
*Pubescence*.—Absent.

Petals:
*Number*.—5.
*Arrangement*.—Free.
*Length*.—Approximately 9 mm.
*Diameter*.—Approximately 6 mm.
*Shape*.—Obovate.
*Apex shape*.—Rounded.

*Base shape*.—Narrows at point of attachment.
*Color of inner and outer surface*.—Approximately White 155D.
*Surface texture*.—Smooth.
*Margins*.—Slightly undulating, entire.
*Frequency of flowers with double petals*.—None.
*Size*.—Medium.
*Claw length*.—Medium, about 1.5 mm.
*Margin waviness*.—Weak.
*Base angle*.—Narrow.
*Division of upper margin*.—Entire.
*Pubescence of inner surface*.—Absent.
*Pubescence of outer surface*.—Absent.

Sepals:
*Number*.—5.
*Length*.—Approximately 3 mm.
*Diameter*.—Approximately 3 mm.
*Shape*.—Triangular.
*Color*.—About Medium Yellow-Green 144A.
*Surface texture*.—Smooth.
*Margins*.—Entire.
*Positioning*.—Adpressed to petals.
*Pubescence of inner surface*.—Absent.
*Pubescence of outer surface*.—Absent.
*Frequency of flowers with double sepals*.—None.

Stamens:
*Number*.—Usually 25-30.
*Average length*.—About 1-10 mm.
*Filament color*.—About White 155D.
*Anther color*.—About Medium Greyed-Yellow 162A.
*Flower pollen color*.—About Medium Greyed-Yellow 162A when dried.
*Position*.—Perigynous.

Pistil:
*Color*.—About Medium Yellow-Green 144B.
*Number*.—Usually one, occasionally two.
*Average length*.—Approximately 6-9 mm.
*Ovary diameter*.—Approximately 1 mm.
*Pubescence*.—None.
*Stigma extension in comparison to anthers*.—Usually below anthers.
*Style frequency of supplementary pistils*.—Few.

Receptacle:
*Depth*.—Medium.
*Pubescence of inner surface*.—Absent.
*Pubescence of outer surface*.—Absent.

Ovary:
*Color*.—About Medium Yellow-Green 144B.
*Pubescence*.—Absent.

Style:
*Color*.—About Medium Yellow-Green 144B.
*Pubescence*.—Absent.

FRUIT

General: (Description taken near Wasco, Kern County, Calif. on August 12).
*Date of first pick*.—Approximately August 8.
*Date of last pick*.—Approximately August 20.
*Maturity when described*.—Firm-mature.
*Season ripening*.—Medium, approximately August 8 to August 20.
*Position of maximum diameter*.—Center.
*Symmetry about the suture*.—Symmetric or slightly assymetric.

Size:
*Length* (*stem end to apex*).—Approximately 75 mm.
*Diameter in line with suture plane*.—Approximately 75 mm.
*Diameter perpendicular to suture plane*.—Approximately 70 mm.
*Average weight*.—Approximately 180 gm.

Form:
*Viewed from apex*.—Rounded.
*Viewed from side, facing suture*.—Rounded, slightly elongated.
*Viewed from side, perpendicular to suture*.—Rounded, slightly elongated.

Apex shape: Rounded.

Fruit stem cavity:
*Shape*.—Elongated in suture plane.
*Depth*.—Shallow; Approximately 0.8 cm.
*Breadth*.—Approximately 1 cm.
*Width*.—Narrow, approximately 1 cm.

Fruit stem:
*Length*.—Medium; approximately 8 mm.
*Diameter*.—Approximately 3 mm.
*Color*.—About Light Yellow-Green 147D.
*Adherence to stone*.—Medium.

Fruit skin:
*Thickness*.—Medium, approximately 0.8 mm.
*Adherence to flesh*.—Medium.
*Surface texture*.—Smooth.
*Pubescence*.—None.
*Bloom*.—Medium-heavy.
*Ground color*.—About Medium Yellow-Green 148B to Medium Greyed-Orange163C.
*Overcolor*.—Dapple, About Dark Greyed-Purple 187B to Dark Greyed-Purple 187A.
*Taste*.—Neutral.
*Reticulation*.—Slight.
*Roughness*.—Absent.
*Tenacity*.—Tenacious to flesh.
*Tendency to crack*.—None in wet season.

Flesh:
*Ripens*.—Evenly.
*Texture*.—Crisp-juicy.
*Fibers*.—Few.
*Flavor*.—Mildly Sweet.
*Brix*.—Approximately 19°.
*Juice*.—Abundant.
*Aroma*.—Slight fruity aroma.
*Color*.—About Dark Red 53A.
*Anthocyanin color of flesh*.—Strongly expressed throughout evenly.
*Acidity*.—Medium.
*Sugar content*.—High.
*Eating quality*.—Good.
*Stone/flesh ratio*.—Small.
*Firmness*.—Medium.

Pit cavity size:
*Length*.—Approximately 25 mm.
*Diameter perpendicular to suture plane*.—Approximately 18 mm.
*Diameter in line with suture*.—Approximately 10 mm.
*Color*.—About Dark Red 53A.

Fruit use: Fresh market.

Fruit shipping and keeping quality: Good.

Stone:
*Stone freeness*.—Cling.
*Degree of adherence to flesh*.—Medium.
*Stone size*.—Size: Medium. Size compared to Fruit: Small. Length: Medium, approximately 25 mm.

Diameter in line with suture plan: Approximately 18 mm. Diameter perpendicular to suture plane: Approximately 10 mm. Width of Stalk End: Medium, Approximately 8 mm. Angle of Stalk end: Right angle. Hilum: Oval.

*Stone form*.—Viewed from side: Oval with flat base. Viewed from ventral end: Flattened. Viewed from Stem end: Oval.

*Stone shape*.—Base shape: Nearly straight. Apex shape: Rounded with small point.

*Stone surface*.—Rough with irregular shallow furrows.

*Stone halves*.—Nearly symmetrical.

*Stone ridges*.—Rough, rounded.

*Stone outgrowing keel*.—Well-developed.

*Stone tendency to split*.—Almost none.

*Stone color*.—About Medium Greyed-Orange 174A.

*Position of maximum*.—Middle.

*Sides*.—Nearly equal.

*Pits*.—Angular.

*Ventrical edge*.—Narrow.

*Dorsal edge*.—Narrow continuous.

What is claimed is:

1. A new and distinct plum tree as herein described and illustrated.

* * * * *

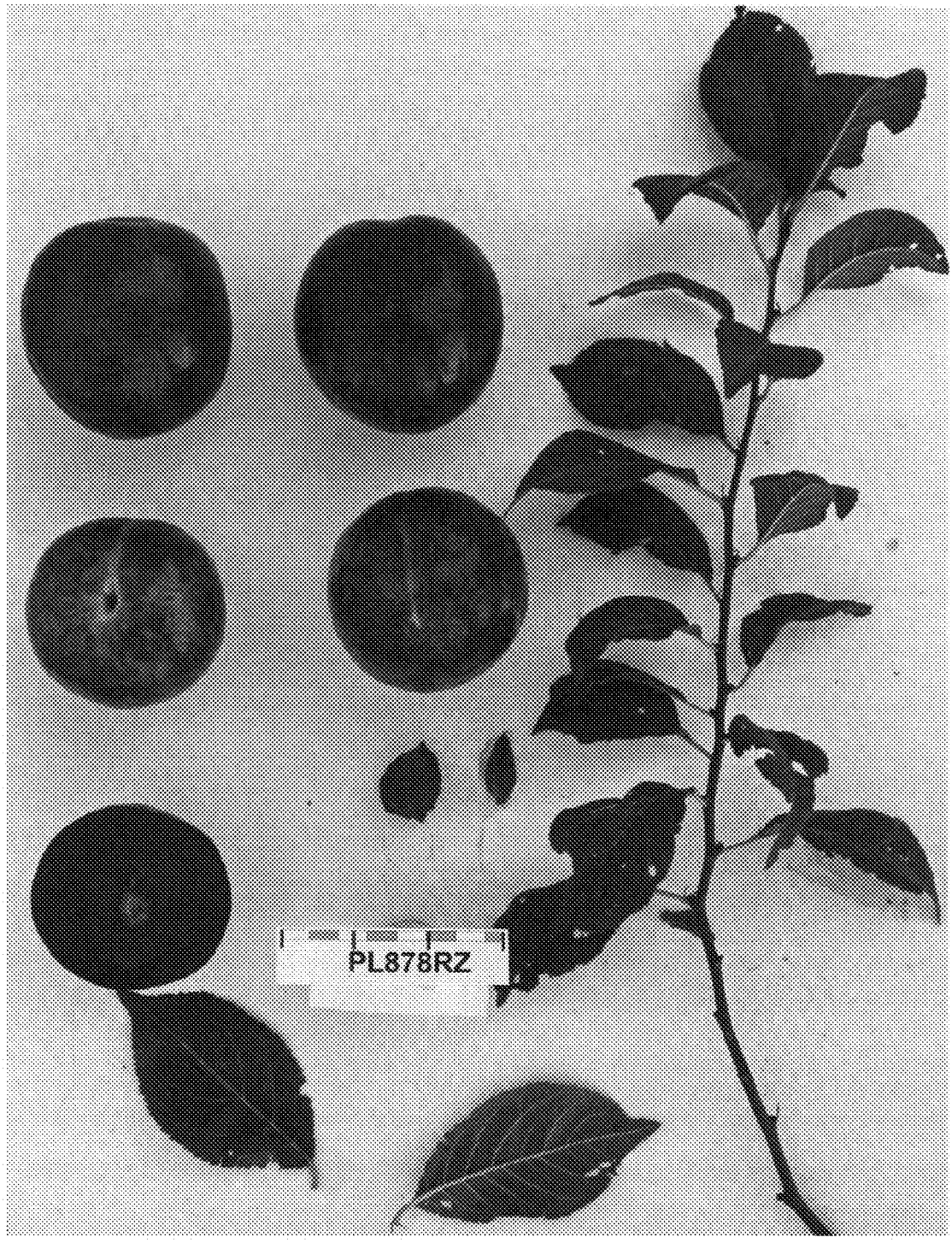
PL878RZ